US012733788B2

(12) United States Patent
Lin et al.

(10) Patent No.: US 12,733,788 B2
(45) Date of Patent: Sep. 15, 2026

(54) MANOMETRY SYSTEMS

(71) Applicant: Covidien LP, Mansfield, MA (US)

(72) Inventors: Jennifer Lin, Broomfield, CO (US); Ryan S. Sohlden, Lyons, CO (US); Aria S.A. Thakore, Superior, CO (US)

(73) Assignee: Covidien LP, Mansfield, MA (US)

(*) Notice: Subject to any disclaimer, the term of this patent is extended or adjusted under 35 U.S.C. 154(b) by 669 days.

(21) Appl. No.: 18/141,517

(22) Filed: May 1, 2023

(65) Prior Publication Data

US 2023/0355076 A1 Nov. 9, 2023

Related U.S. Application Data

(60) Provisional application No. 63/338,579, filed on May 5, 2022.

(51) Int. Cl.

*A61B 1/00* (2006.01)
*A61B 1/005* (2006.01)
*A61B 1/273* (2006.01)

(52) U.S. Cl.

CPC ...... *A61B 1/00016* (2013.01); *A61B 1/00006* (2013.01); *A61B 1/00045* (2013.01); *A61B 1/00147* (2013.01); *A61B 1/005* (2013.01); *A61B 1/2736* (2013.01)

(58) Field of Classification Search

CPC ............ A61B 1/00016; A61B 1/00006; A61B 1/00045; A61B 1/00147; A61B 1/005; A61B 1/2736; A61B 5/037; A61B 5/6853; A61B 5/42

See application file for complete search history.

(56) References Cited

U.S. PATENT DOCUMENTS 7,862,502 B2 * 1/2011 Pool ...................... A61F 5/0053 600/37
8,246,533 B2 * 8/2012 Chang ................ A61B 17/3417 600/37
8,706,208 B2 * 4/2014 Chiao .................. A61B 5/0031 600/350

(Continued)

FOREIGN PATENT DOCUMENTS

CN 105473167 A * 4/2016 ............. A61B 90/70
WO WO-2018055487 A1 * 3/2018 ........... A61B 5/6861

(Continued)

OTHER PUBLICATIONS

Tutuian R, Castell DO, “Advanced And Cost-Efficient High Resolution Manometry”, Quickview Data Analysis Program 3D Esophageal Pressure Topography Latest Chicago Classification Economical And Customizable, American Journal of Gastroenterology, 2004, 2:230-236 (2019).

*Primary Examiner* — Jeffrey G. Hoekstra
(74) *Attorney, Agent, or Firm* — Carter, DeLuca & Farrell, LLP

(57) ABSTRACT

A manometry system includes a manometric catheter configured to sense pressure within a gastrointestinal tract, a computer in communication with the catheter, and a display. The manometric system may further include at least one of a remote controller configured to couple to the catheter, a strap configured to secure the catheter to a patient’s head, or an RFID scanner configured to sense a location of one or more RFID tags attached to or embedded in the catheter.

17 Claims, 9 Drawing Sheets

(56) References Cited

U.S. PATENT DOCUMENTS

| | | | |
|---|---|---|---|
| 10,052,082 B2 | 8/2018 | Hossack et al. | |
| 10,278,780 B2 * | 5/2019 | Shelton, IV | A61B 17/07207 |
| 11,246,694 B2 * | 2/2022 | Cheng | A61B 17/7216 |
| 11,291,441 B2 * | 4/2022 | Giordano | A61B 17/320092 |
| 2014/0288612 A1 * | 9/2014 | Addington | A61B 5/113 607/48 |
| 2020/0237242 A1 * | 7/2020 | Kaluzny | H02J 7/0013 |
| 2022/0047339 A1 * | 2/2022 | Prior | A61B 34/76 |
| 2023/0355076 A1 * | 11/2023 | Lin | A61B 1/00016 |

FOREIGN PATENT DOCUMENTS

| | | | |
|---|---|---|---|
| WO | WO-2020033263 A1 * | 2/2020 | C12Q 1/04 |
| WO | WO-2020087043 A1 * | 4/2020 | G01N 21/51 |
| WO | WO-2020160001 A1 * | 8/2020 | A61B 5/6852 |
| WO | WO-2020191194 A1 * | 9/2020 | A61L 9/015 |
| WO | WO-2020257560 A1 * | 12/2020 | A61B 5/6853 |

* cited by examiner

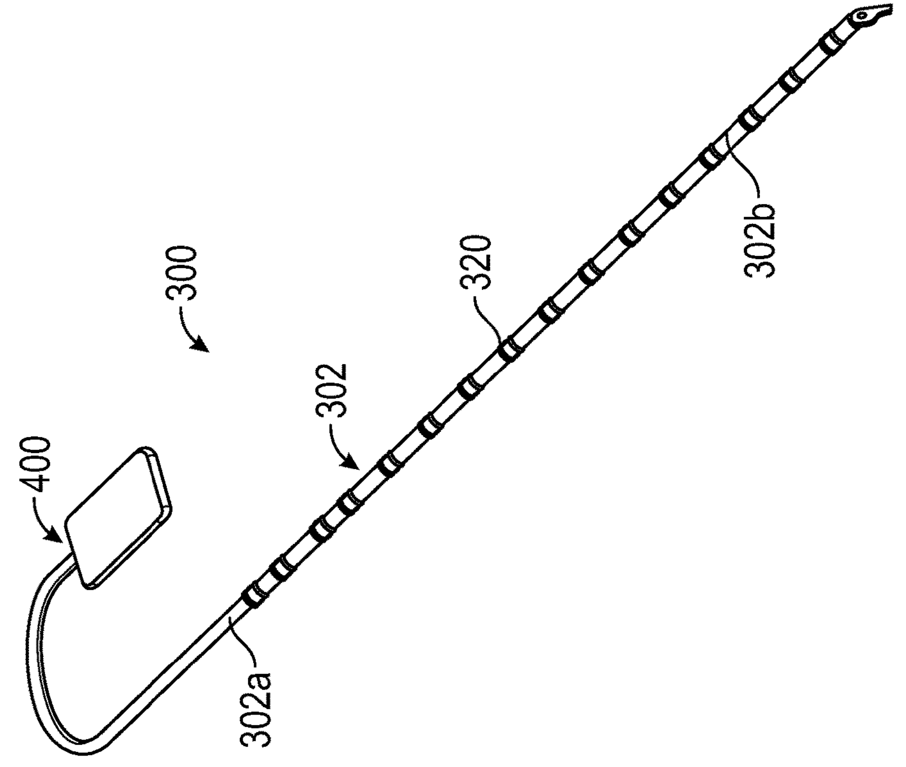
FIG. 1
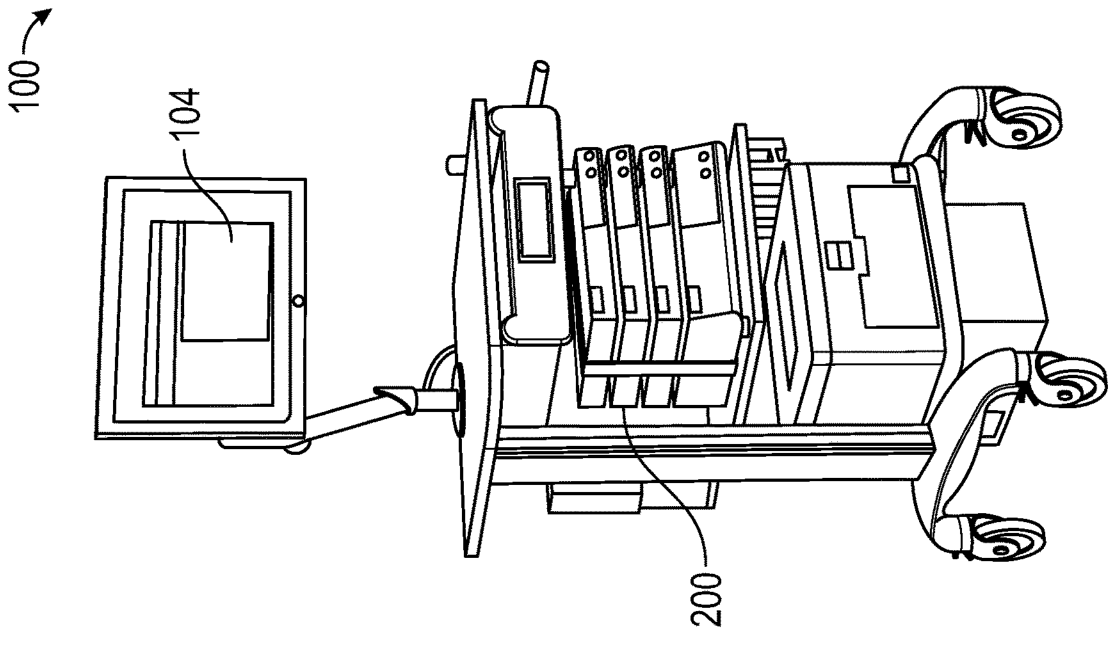

MANOMETRY SYSTEMS

CROSS-REFERENCE TO RELATED APPLICATIONS

This application claims the benefit of the filing date of provisional U.S. Patent Application No. 63/338,579 filed on May 5, 2022.

FIELD

This disclosure relates generally to diagnostic instruments, and more particularly, to a manometry system.

BACKGROUND

The esophagus is a tubular organ that carries food and liquid from the throat to the stomach. Accurate measurements of physiological parameters of the esophagus under realistic swallowing conditions are valuable in diagnosing esophageal diseases such as achalasia, dysphagia, diffuse esophageal spasm, ineffective esophageal motility, and hypertensive lower esophageal sphincter (LES). When a person with a healthy esophagus swallows, circular muscles in the esophagus contract. The contractions begin at the upper end of the esophagus and propagate downwardly toward the lower esophageal sphincter (LES). The function of the peristaltic muscle contractions, i.e., to propel food and drinks through the esophagus to the stomach, is sometimes called the motility function, but is also often referred to as peristalsis.

Esophageal manometry, in particular, is a test used to assess pressure and motor function of the esophagus, allowing physicians to evaluate how well the muscles in the esophagus work to transport liquids or food from the mouth into the stomach.

SUMMARY

In accordance with the disclosure, a manometry system is provided that includes a manometric catheter, one or more RFID tags, and an RFID scanner. The catheter includes a flexible, elongated body having a proximal end portion, and a distal end portion configured for receipt in a gastrointestinal (GI) tract of a patient. A plurality of pressure sensors is positioned along a length of the elongated body. The RFID tag is coupled to the distal end portion of the elongated body, and the RFID scanner is configured to detect the RFID tag of the manometric catheter.

In aspects, a plurality of RFID tags is positioned along a length of the distal end portion of the elongated body.

In aspects, each of the plurality of RFID tags may have a unique ID.

In aspects, the RFID scanner may be a patch or a belt configured to be secured to an external surface of a patient.

In aspects, the belt may include a plurality of RFID sensors positioned along a length of the belt, and the plurality of RFID sensors may be configured to output a signal in response to sensing the respective RFID tag.

In aspects, the manometry system may further include a display in communication with the RFID scanner. The display may be configured to receive the signals output from the plurality of RFID sensors of the RFID scanner and display a progress of an insertion of the catheter within the GI tract.

In aspects, the manometry system may further include a processor, and a memory, including instructions stored thereon, which, when executed, cause the manometry system to: acquire a pressure measurement from each of the plurality of pressure sensors; and assess, based on the pressure measurements, at least one of a motility function of an esophagus or a bolus transit dynamics in the esophagus.

In aspects, the catheter may further include a remote controller configured to be in communication with the processor. The remote controller may have an actuator configured to actuate functions of the manometry system.

In aspects, the remote controller may include a user interface display.

In aspects, the manometry system may further include a flexible strap configured to secure the proximal end portion of the catheter to a head of a patient.

BRIEF DESCRIPTION OF DRAWINGS

Various aspects of the disclosure are described herein with reference to the drawings wherein:

FIG. 1 is a perspective view illustrating a manometry system including a control station and a catheter in accordance with the disclosure;

DETAILED DESCRIPTION

Figure 2:
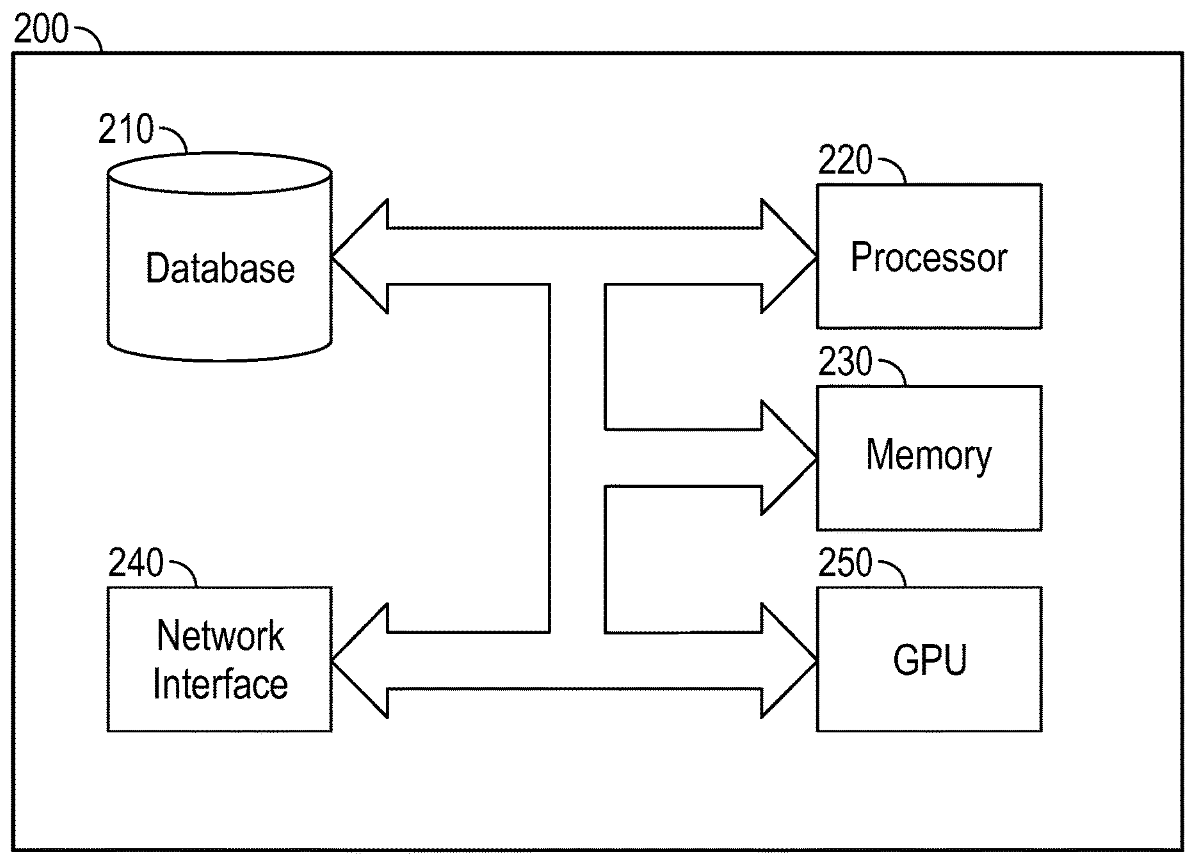
FIG. 2 is a block diagram illustrating the controller of the manometry system of FIG. 1.

The disclosed manometry system and components thereof will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

Esophageal manometry, in particular, is a test used to assess pressure and motor function of the esophagus, allowing physicians to evaluate how well the muscles in the esophagus work to transport liquids or food from the mouth into the stomach. To perform this test, the manometry system operates in conjunction with a manometric catheter placed in the esophagus of a patient to record pressure and/or impedance data over a period of time using various sensors placed on the catheter. The data is analyzed using analysis software to evaluate causes of, and help diagnose conditions such as, gastric reflux, dysphagia, functional chest pain, achalasia, and hiatal hernia.

The manometry system obtains high resolution and/or three-dimensional (3D) mapping of pressure levels within the tubular organs of the human gastrointestinal tract and, optionally, pressure with impedance levels within the tubular organs of the human upper gastrointestinal tract which may include the pharynx, esophagus, proximal gut (stomach/duodenum), anus, and rectum. The manometry system is used in a medical clinical setting to acquire the pressure and impedance levels and store the corresponding data for visualization and analysis using the software. Esophageal manometry is used as an example; the systems and methods of the disclosure are applicable to other forms of manometry systems, for example, a rectal manometry system.

FIG. 1 illustrates a manometry system 100. The manometry system 100 generally includes: a control station including a controller 200 and a display 104; and a manometric catheter or probe 300. The controller 200 (FIG. 2) is configured to execute software for data acquisition and analysis. Various manometric catheter 300 configurations may be used depending on the application (esophageal/anorectal manometry), size, and catheter diameter.

The manometry system 100 enables full evaluation of the motor functions of an esophagus. The system 100 allows for enhanced sensitivity that provides useful information to support diagnosis of conditions like dysphagia, achalasia, and hiatal hernia. By precisely quantifying the contractions of the esophagus and its sphincters, this procedure helps provide a more complete esophageal pressure profile of the patient.

Esophageal pressure measurement, or manometry, as well as electrical impedance, can be used to assess motility function of the esophagus and bolus transit dynamics in the esophagus. The manometric catheter 300 includes a plurality of sensor assemblies 320 (e.g., pressure sensors) located along its length. The manometric catheter 300 may be inserted into the esophagus, typically reaching the lower esophageal sphincter (LES) and extending into the stomach of a patient, with the pressure sensors 320 positioned at the LES and at a plurality of other specific points along the length of the esophagus at predetermined distances above the LES. The LES is a muscle that separates the esophagus from the stomach. It acts as a valve that normally stays tightly closed to prevent contents in the stomach from backing up into the esophagus During a procedure, the patient swallows (e.g., with or without liquid) with the manometric catheter 300 placed in the esophagus. The esophageal pressure at the sensor assemblies 320 can be measured and used as an indication of the magnitude and sequence of the peristaltic contractions. In addition, because the positions of the sensor assemblies 320 are known, the velocity of the peristaltic motion can also be ascertained from the location of the peak pressure, or onset of pressure rise, at each location as a function of time. The test can be repeated a number of times to obtain a set of pressure and velocity values, a statistical analysis of which may be used for diagnostic purposes.

High-resolution manometry involves the collection of data with a catheter having closely spaced sensors. Such high-resolution data enables spatiotemporal contour plots visualization of contractile pressure physiology. Products such as ManoScan™ data acquisition software and ManoView™ data analysis software may be used to aid in acquiring and visualizing high-resolution manometry data.

The manometric catheter 300 may include other sensors (not explicitly shown) such as impedance sensors. High-resolution impedance measurements provide for spatiotemporal plotting of bolus movement. Electrical impedance at a plurality of points in the esophagus can be used to detect and monitor the movement of a bolus through the esophagus. A bolus of water or food will have different electrical impedance than the non-filled esophagus, so a change in impedance in the esophagus indicates the presence of a bolus. Therefore, the manometric catheter 300 positioned in the esophagus with a plurality of impedance and/or acidity sensors dispersed along its length can be used to detect and monitor the bolus transit, i.e., the movement of a bolus through the esophagus.

FIG. 2 illustrates the controller 200, in accordance with the disclosure, which includes a processor 220 that is connected to a computer-readable storage medium or a memory 230. The computer-readable storage medium or memory 230 may be a volatile type memory, e.g., RAM, or a non-volatile type memory, e.g., flash media, disk media, etc. In various aspects of the disclosure, the processor 220 may be any suitable type of processor such as, without limitation, a digital signal processor, a microprocessor, an ASIC, a field-programmable gate array (FPGA), or a central processing unit (CPU).

In aspects of the disclosure, the memory 230 can be random access memory, read-only memory, magnetic disk memory, solid-state memory, optical disc memory, and/or another type of memory. In some aspects of the disclosure, the memory 230 can be separate from the controller 200 and can communicate with the processor 220 through communication buses of a circuit board and/or through communication cables such as serial ATA cables or other types of cables. The memory 230 includes computer-readable instructions that are executable by the processor 220 to operate the controller 200. The memory 230 may include volatile (e.g., RAM) and non-volatile storage configured to store data, including software instructions for operating the manometry system 100. In other aspects of the disclosure, the controller 200 may include a network interface 240 to communicate with other computers or to a server. A storage device 210 may be used for storing data.

Figure 3:
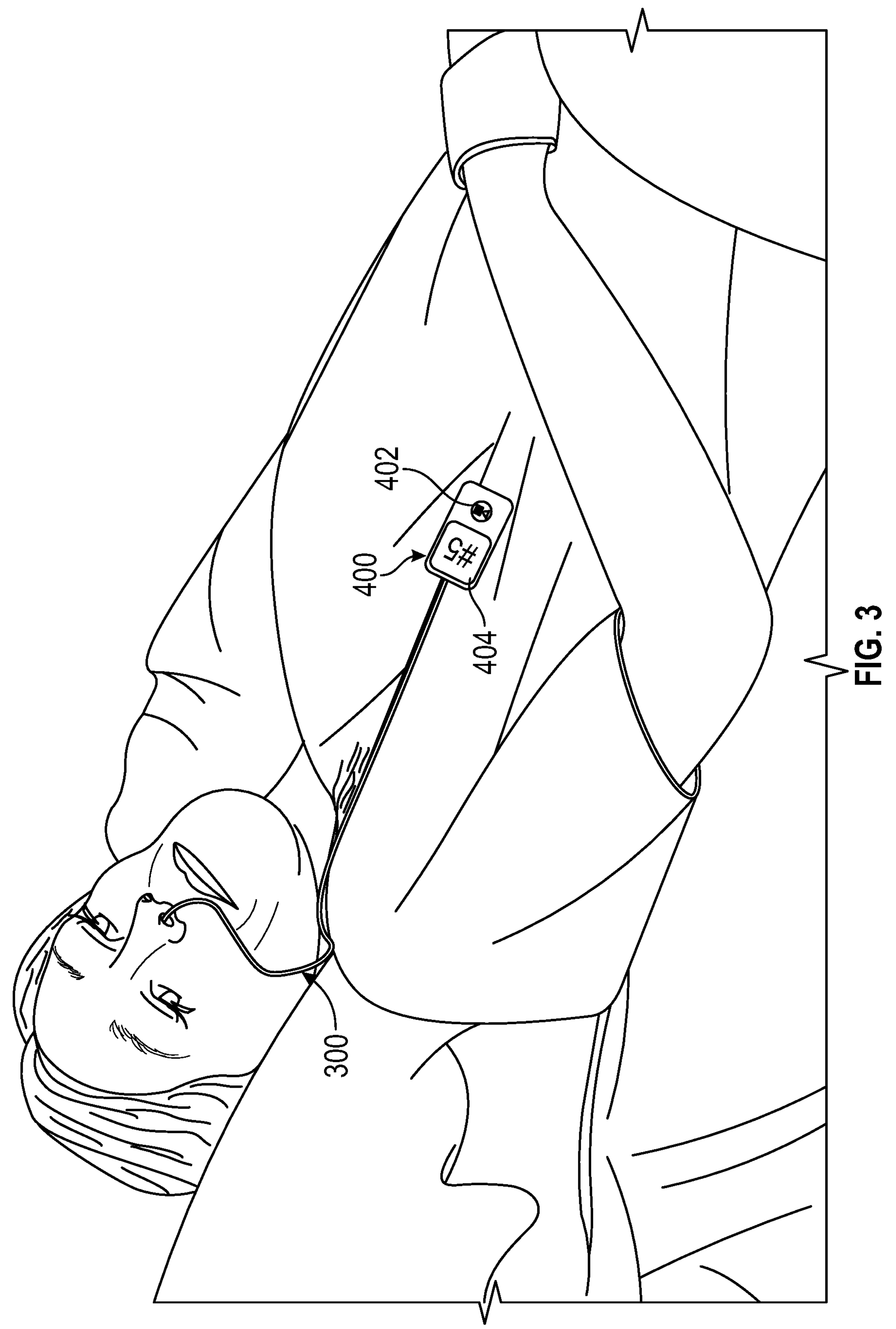
FIG. 3 is a perspective view illustrating one aspect of a manometric catheter, including a remote controller, inserted into a patient.
Figures 4, 5, 6A, 6B:
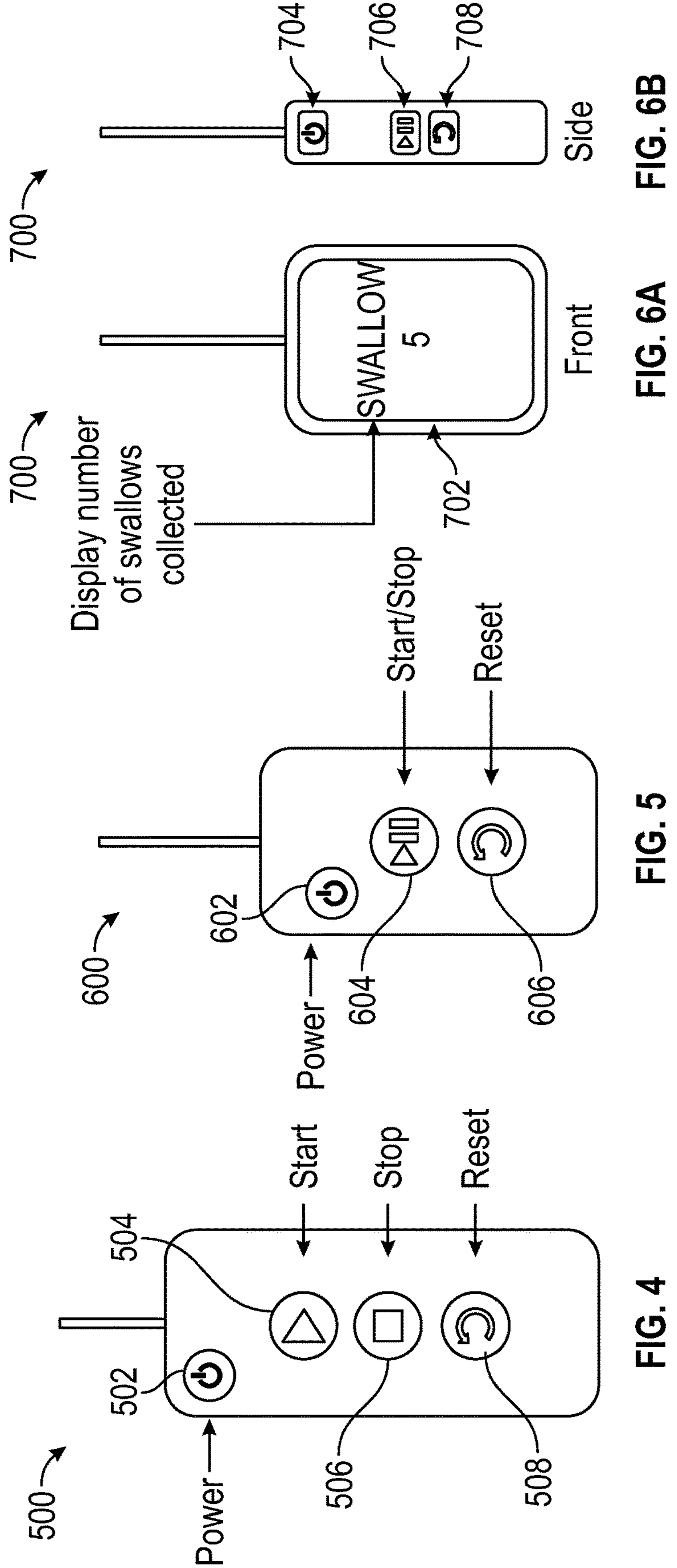
FIG. 4 is a front view illustrating one aspect of a remote controller for use with the catheter of FIG. 3.
FIG. 5 is a front view illustrating another aspect of a remote controller for use with the catheter of FIG. 3.
FIG. 6A is a front view illustrating yet another aspect of a remote controller for use with the catheter of FIG. 3.
FIG. 6B is a side view illustrating the remote controller of FIG. 6A.

With reference to FIGS. 1 and 3, the catheter 300 includes a flexible, elongated body 302 and the plurality of pressure sensors 320. The elongated body 302 of the catheter 300 has a proximal end portion 302*a* configured to be external of a patient, and a distal end portion 302*b* configured to be inserted within a gastrointestinal (GI) tract of a patient. The pressure sensors 320 are positioned along a length of the distal end portion 302*b* of the elongated body 302 in axially-spaced relation from one another. The catheter 300 may further include a remote controller 400, such as, for example, a dongle, detachably coupled to or formed with the proximal end portion 302*a* of the elongated body 302.

The remote controller 400 may be a Bluetooth-enabled dongle. In aspects, the remote controller 400 may be detachably coupled to the proximal end portion 302*a* of the elongated body 302 of the catheter 300 and configured to wirelessly communicate with the controller 200 and/or display 104 (FIG. 1) of the manometry system 100. In aspects, the remote controller 400 may be configured to wirelessly communicate with the components of the manometry system 100 using various radio frequency protocols such as near field communication, radio frequency identification "RFID," BLUETOOTH®, etc. In other aspects, the remote controller 400 may be configured to connect to the controller 200 and/or display 104 via a wire (not shown) or by receiving a port from the controller 200.

With reference to FIG. 3, the remote controller 400 of the catheter 300 is configured to be hand-held and operable by a clinician during a manometry procedure to allow for remote communication with the controller 200 (FIG. 1) by the clinician. The remote controller 400 may include actuators, such as, for example, at least one depressible button 402, configured to allow the user to start, stop, and reset a swallow recording measurement, as well as add indicators along the swallow pattern time graph. The remote controller 400 may further include a display screen 404 that may display, for example, the number of acceptable swallows collected during the procedure by receiving the count from the controller 200 or by tallying the number of swallows based on the number of times the actuator 402 is depressed by the clinician.

The remote controller 400 improves the user experience as the clinician may focus on the recording procedure and the patient at the same time. As such, clinicians will have more flexibility and mobility by isolating the recording activity. The remote controller 400 also improves the patient experience as the clinician can focus more on the patient's needs and experiences. Furthermore, the remote controller 400 may be easily wiped and cleaned after the procedure, which minimizes the number of user touchpoints, and therefore minimizes the potential for contamination by fluids from the patient to the ManoScan™ data acquisition software and ManoView™ data analysis software.

FIGS. 4-6B illustrates alternative aspects of remote controllers 500, 600, 700 for attachment to the catheter 300 of FIG. 1. The remote controller 500 of FIG. 4 includes a power button 502, a start button 504, a stop button 506, and a reset button 508. The remote controller 600 of FIG. 5 includes a power button 602, a start/stop button 604, and a reset button 606. The remote controller 700 of FIGS. 6A and 6B include a display screen 702 positioned on a front side of the remote controller 700, and a power button 704, a start/stop button 706, and a reset button 708 each positioned on a lateral side of the remote controller 700.

Figure 7A:
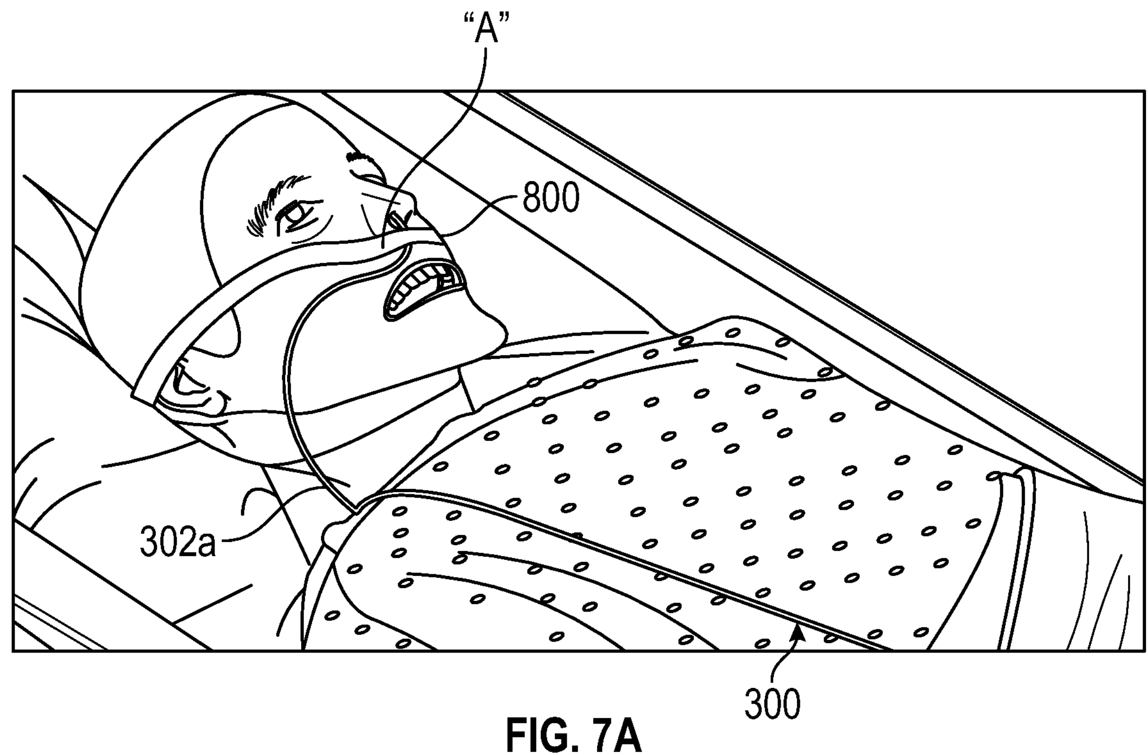
FIG. 7A is a perspective view illustrating an aspect of a strap shown securing a manometric catheter to a patient.
Figure 7B:
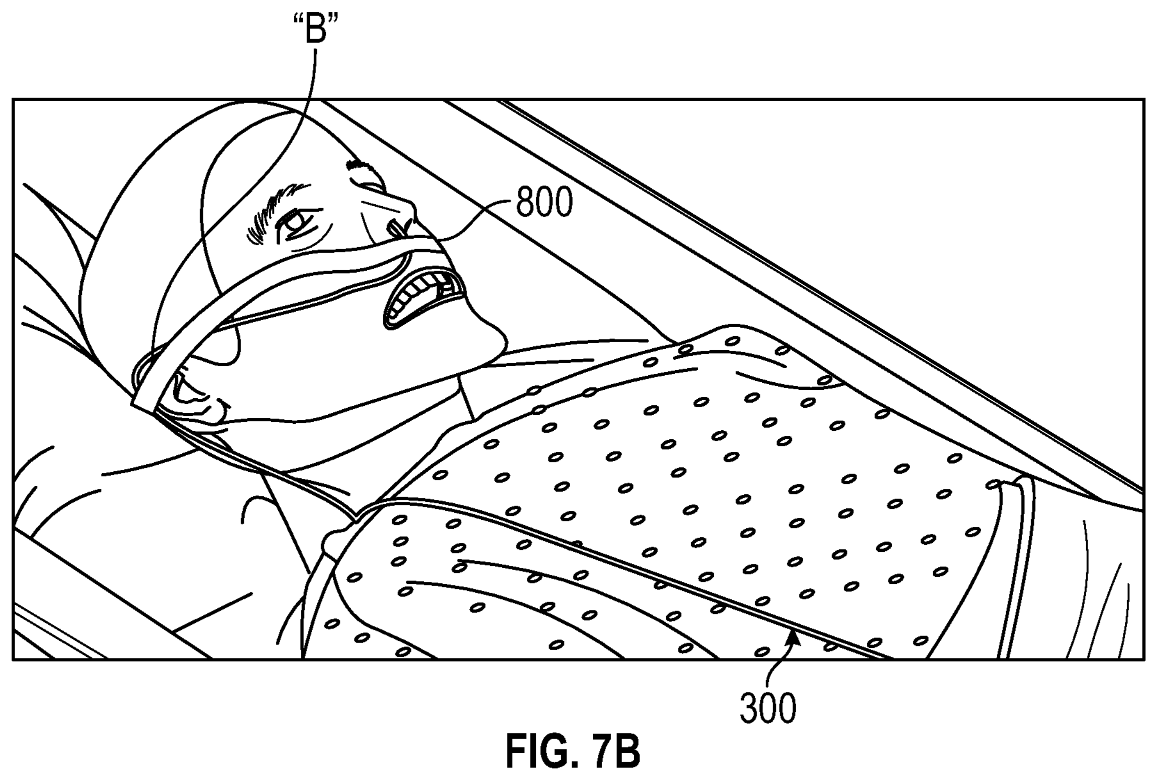
FIG. 7B is a perspective view illustrating the strap of FIG. 7A securing the catheter to the patient in an alternative manner.

With reference to FIGS. 7A and 7B, the manometry system 100 (FIG. 1) may further include a coupling device, such as, for example, a band or strap 800 configured to secure the proximal end portion 302*a* of the elongated body 302 of the catheter 300 to a patient. More specifically, the strap 800 may be single-use or reusable and is fabricated from a flexible material, such as, for example, an elastomer. The strap 800 has a looped configuration such that the strap 800 is configured to encircle a patient's head.

In use, with the proximal end portion 302*a* of the elongated body 302 of the catheter 300 extending from the patient's nostril, as shown in FIG. 7A, the strap 800 may be positioned about the patient's head and over a portion "A" of the catheter 300 that is adjacent the patient's nostril/upper lip. As shown in FIG. 7B, the strap 800 may also be positioned over a portion "B" of the catheter 300 that is positioned over the patient's ear.

Typically, it was challenging for clinicians to efficiently place and assess placement of the catheter 300 to ensure accuracy. Once the catheter 300 was placed and placement was validated, the clinician secured the catheter 300 with tape on the patient's face. Using this method was not foolproof because the catheter 300 may be dislodged with movement or moisture on the patient's face from mucus, tears, and/or saliva. The tape sometimes caused discomfort for the patient. As such, the strap 800, as a replacement for the tape, enables the clinician to secure the catheter 300 without risk of movement in the esophagus. If there is an unusual event (e.g., coughing, choking, etc.), the risk of dislodgment of the catheter 300 will be minimized due to the strap 800.

FIGS. 8-11 illustrate a plurality of types of catheter guidance systems incorporated into the overall manometry system of FIG. 1 configured to assist a clinician in properly guiding and placing a catheter in the desired location within a gastrointestinal (GI) tract of a patient.

Figure 8:
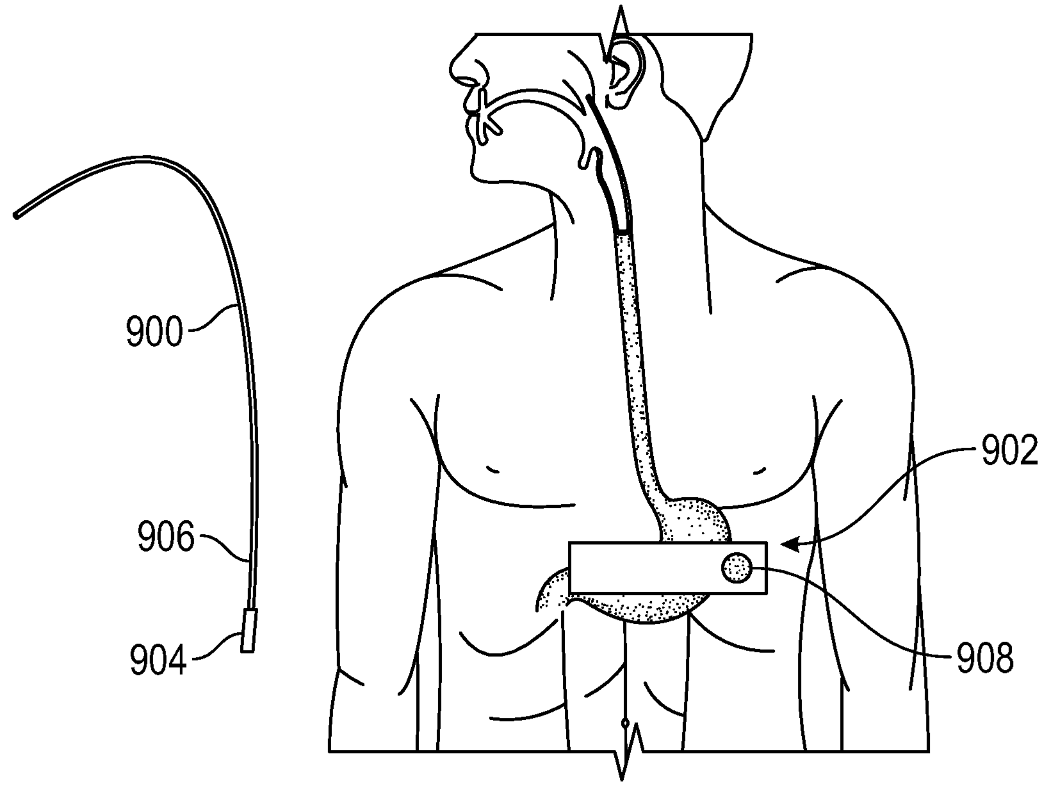
FIG. 8 is a front view illustrating another aspect of a manometric catheter and an RFID patch secured externally to a patient.

With specific reference to FIG. 8, one aspect of a catheter guidance system includes a catheter 900, similar to the catheter 300 of FIG. 1, and a patch 902. The catheter 900 includes a tag 904 secured to a distal end 906 of the catheter 900. In aspects, the tag 904 may be positioned at any suitable location of the catheter 900. The tag 904 may be a radio frequency identification device ("RFID") tag, a near-field communication ("NFC") tag, a Bluetooth tag, or the like.

The patch 902 may be an RFID scanner having an RFID sensor (not explicitly shown) configured to sense or detect the presence of the RFID tag 904 of the catheter 900 when the RFID tag 904 is within a threshold distance from the patch 902, such as, for example, a typical distance from a stomach of a patient to an external surface of the patient's abdomen directly over the stomach. The patch 902 may include evenly-distributed, radiolucent antennae configured to sense signals emitted by the RFID tag 904. The patch 902 may include a light 908, such as, for example, an LED, configured to illuminate when the patch 902 detects the presence of the RFID tag 904 of the catheter 900. Additionally or alternatively, the patch 902 may include a speaker (not explicitly shown) configured to produce an auditory alert both when the patch 902 detects the presence of the RFID tag 904 and when the signals from the RFID tag 904 cease to be received by the patch 902.

In operation, a clinician applies the patch 902 at a selected location external of the patient, for example, on the skin of the abdomen known to be overlapping with the patient's stomach or a selected portion of the stomach. The catheter 900, with the RFID tag 904 secured thereto, is inserted into the patient's nostril and distally through the esophagus. While the catheter 900 is being passed down the esophagus, the clinician may monitor the patch 902 to verify whether the distal end 906 of the catheter 900 has reached a preselected end location within the GI tract (e.g., the stomach). When the RFID tag 904 of the catheter 904 is at the desired location, and therefore in overlapping alignment with the patch 902, the RFID sensor of the patch 902 detects the RFID tag 904 and alerts the clinician (e.g., visually or audibly) that the catheter 900 is in the correct position. The catheter 900 may then be secured in place, e.g., utilizing the strap 800 (FIGS. 7A-7B). It is contemplated that the clinician may monitor the patch 902 while the manometry procedure is being performed to continuously verify whether the catheter 900 is maintained in the correct position as a patient is prompted to swallow.

Figure 9:
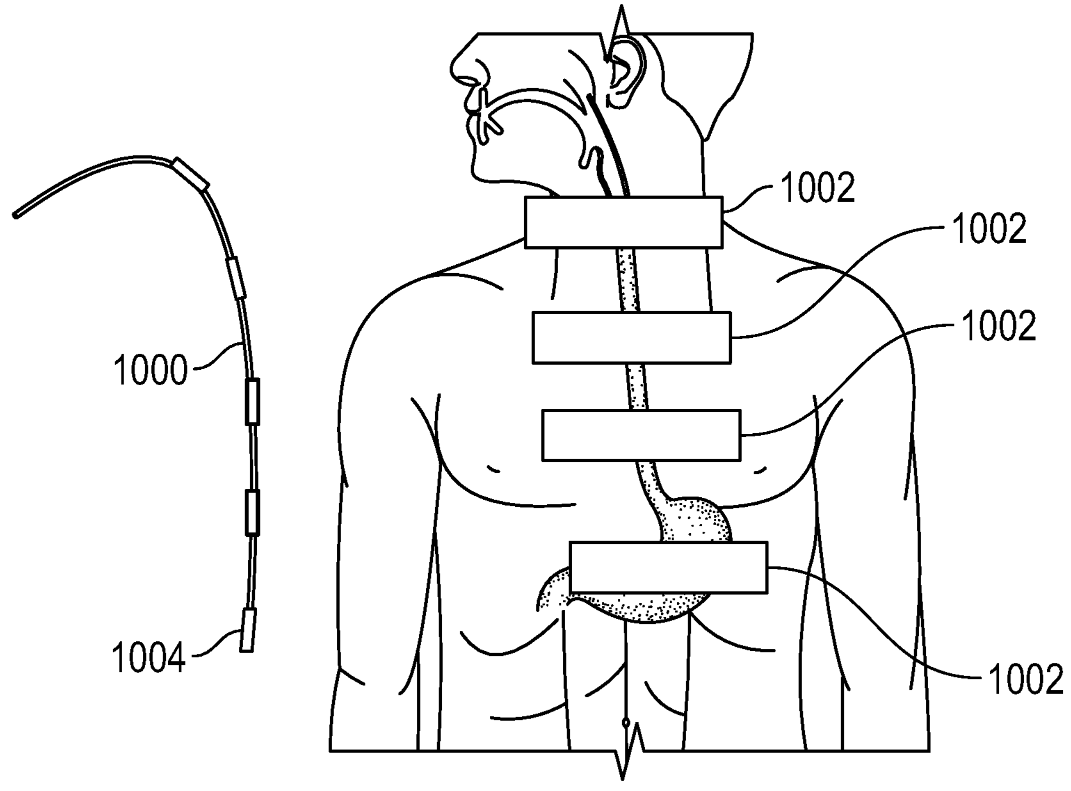
FIG. 9 is a front view illustrating another aspect of a manometric catheter and a plurality of RFID patches secured externally to a patient.

With reference to FIG. 9, another aspect of a catheter guidance system for incorporation into the manometry system 100 (FIG. 1) includes a catheter 1000, similar to the catheter 900 of FIG. 1, and a plurality of patches 1002, each being similar to patch 902 of FIG. 8. The catheter 1000 includes a plurality of tags or sensors 1004, such as the RFID sensor 904 described with reference to FIG. 8. The RFID sensors 1004 are positioned along a length of the catheter 1000 and axially spaced from one another a suitable, predetermined distance. Each of the patches 1002 are configured to sense or detect the presence of the RFID tags 1004 of the catheter 1000 when the respective RFID tag 1004 is within a threshold distance from the RFID patch 1004. The patches 1002 are in communication (e.g., wireless or wired) with the controller 200 (FIG. 1) and configured to output a signal to the controller 200 and/or display 104 when the respective patch 1002 detects the presence of the RFID tag 1004.

The patches 1002 may each output a signal when the patches 1002 receive a signal from the respective RFID tag 1004. When all of the patches 1002 are outputting a signal to the controller 200, the controller 200 is configured to determine that the catheter 1000 is correctly placed. On the other hand, if only some of the patches 1002 are outputting a signal to the controller 200, the controller 200 may be configured to determine that the catheter 1000 is incorrectly placed (e.g., bent).

In operation, a clinician applies the patches 1002 at selected locations external of the patient, for example, on the skin of the chest and abdomen known to be overlapping with the patient's esophagus and stomach. The catheter 1000, with the RFID tags 1004 secured thereto, is inserted into the patient's nostril and distally through the esophagus. As the catheter 1000 is passed down the esophagus, each patch 1002 may illuminate as the RFID tag 1004 passes over the respective patch 1002 to allow the clinician to monitor the progress of the catheter 1000 insertion.

In aspects, the display 104 (FIG. 1) of the manometry system 100 may show a graphic of the insertion based on the information received by the patches 1002. When the distal-most RFID tag 1004 of the catheter 1000 is at the desired location (e.g., the stomach), and therefore in overlapping alignment with the distal-most patch 1002, the clinician will know that the catheter 1000 is in the correct position. The catheter 1000 may then be secured in place, e.g., utilizing the strap 800 (FIGS. 7A-7B). It is contemplated that the clinician may monitor the patches 1002 and/or the display 104 (FIG. 1) while the manometry procedure is being performed to continuously verify whether the catheter 1000 is maintained in the correct position.

Figure 10:
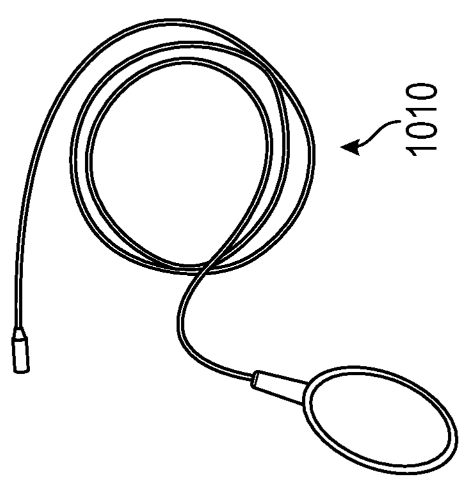
FIG. 10 is a front view illustrating the manometric catheter of FIG. 9 and an RFID scanner.
Figure 10:
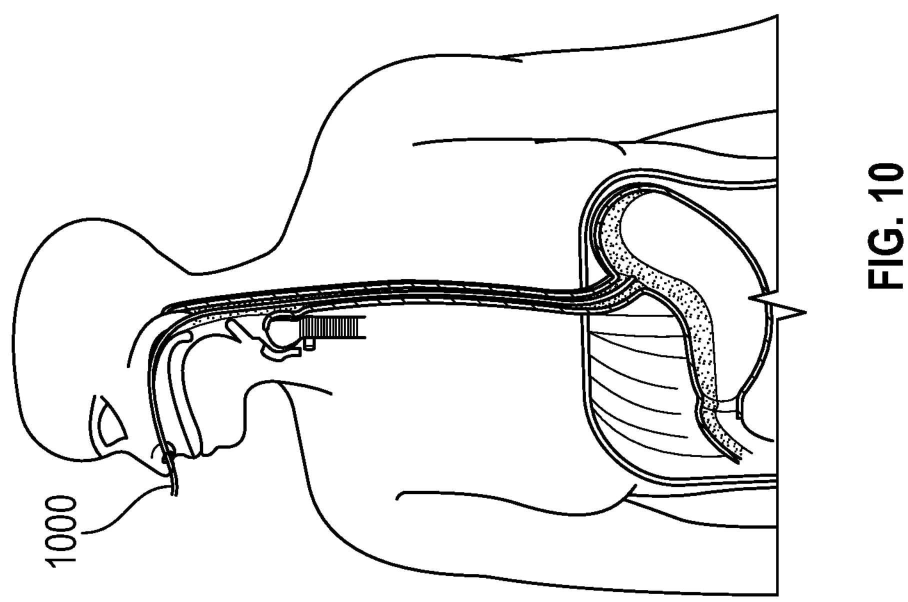
Figure 10:
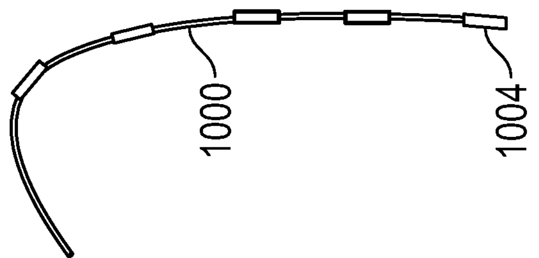

With reference to FIG. 10, another aspect of a catheter guidance system for incorporation into the manometry system 100 of FIG. 1 includes the catheter 1000 and a hand-held scanning device, such as, for example, an RFID scanner 1010. The RFID scanner 1010 may be in communication with the controller 200 (FIG. 1) and/or the RFID scanner 1010 may include a user interface display.

In operation, the catheter 1000, with the RFID tags 1004 secured thereto, is inserted into the patient's nostril and distally through the esophagus. As the catheter 1000 is passed down the esophagus, the clinician positions the RFID scanner 1010 over the area of the patient's body where the clinician believes the catheter 1000 to be located. The RFID scanner 1010 may provide a visual or audible indication when each RFID tag 1004 of the catheter 1000 passes near the RFID scanner 1010 to allow the clinician to monitor the progress of the catheter 1000 insertion. In aspects, the display 104 (FIG. 1) of the manometry system 100 may show a graphic of the insertion based on the information received by the RFID scanner 1010. When the catheter 1000 is determined to be properly placed, based on the information provided by the RFID scanner 1010, the catheter 1000 may be secured in place, e.g., utilizing the strap 800 (FIGS. 7A-7B). It is contemplated that the clinician may continuously verify whether the catheter 1000 is maintained in the correct position during the manometry procedure by utilizing the RFID scanner 1010.

Figure 11:
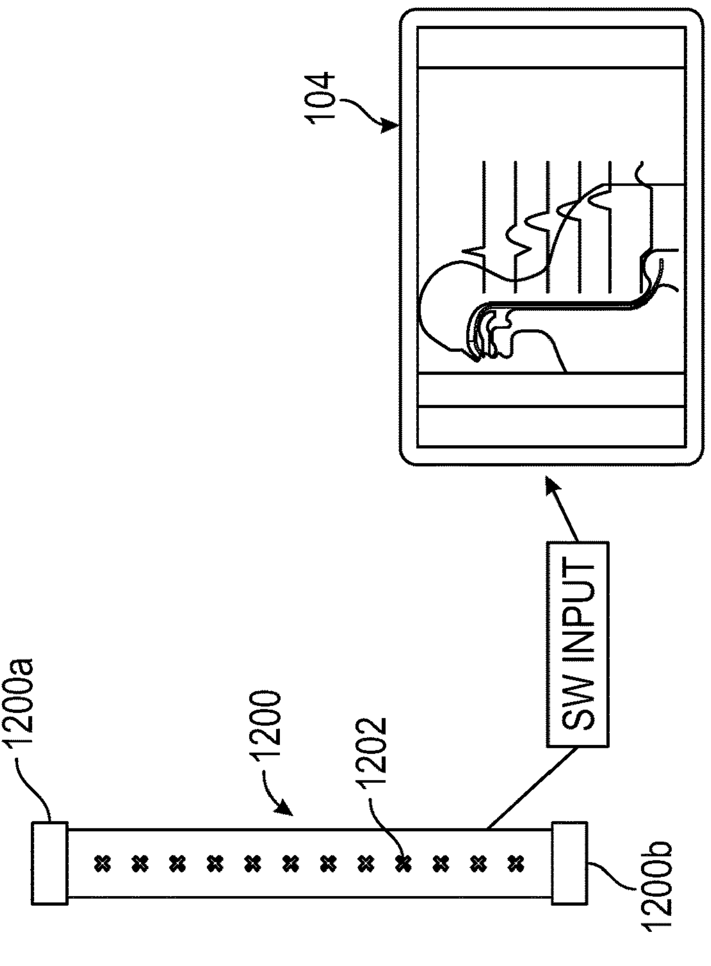
FIG. 11 is a front view illustrating the manometric catheter of FIG. 9 used in conjunction with an RFID belt and a user interface display of the system of FIG. 1.
Figure 11:
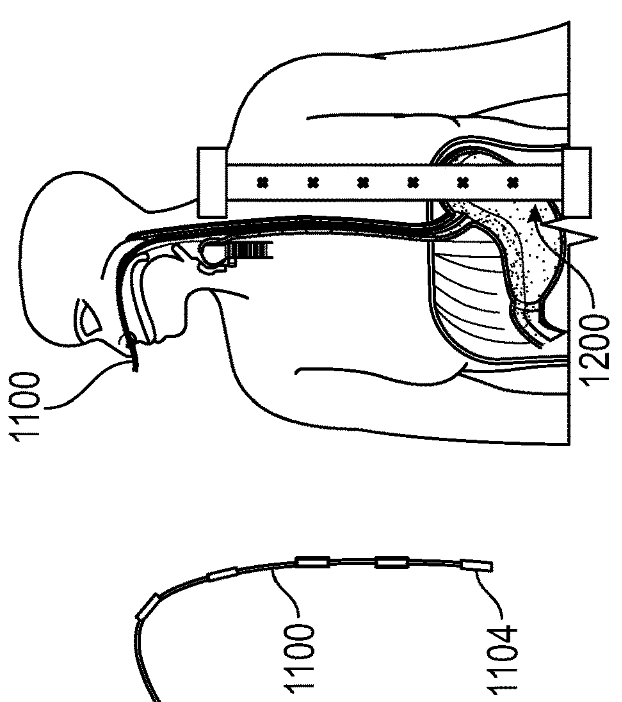

With reference to FIG. 11, another aspect of a catheter guidance system for incorporation into the manometry system 100 of FIG. 1 includes a catheter 1100, similar to the catheter 1000 of FIG. 10, and a belt 1200. The catheter 1100 includes a plurality of tags or sensors 1104, such as a plurality of RFID sensors 1104 with each having a unique ID. The RFID sensors 1104 are positioned along a length of the catheter 1100 and axially spaced from one another a suitable, predetermined distance.

The belt 1200 may have a length approximating a length of an esophagus and have opposing first and second ends 1200*a* configured to secure to a patient using, for example, tape, adhesive, or the like. The belt 1200 includes a plurality of sensors, such as, for example, RFID sensors 1202, configured to sense or detect the presence of the RFID tags 1104 of the catheter 1100 when the respective RFID tag 1104 is within a threshold distance from the respective RFID sensor 1202. The RFID sensors 1202 are positioned along a length of the belt 1200 and axially spaced from one another. In aspects, the RFID sensors 1202 are in communication (e.g., wireless or wired) with the controller 200 (FIG. 1) and are configured to output a signal to the controller 200 and/or display 104 when the respective RFID sensor 1202 detects the presence of the RFID tag 1104 in addition to the location of the RFID tag 1104.

In operation, a clinician applies the belt 1200 external of the patient, for example, on the skin of the chest and abdomen known to be overlapping with the patient's esophagus and stomach. The catheter 1100, with the RFID tags 1104 secured thereto, is inserted into the patient's nostril and distally through the esophagus. As the catheter 1100 is passed down the esophagus, the RFID sensors 1202 of the belt 1200 may illuminate as the RFID tag 1104 passes over the respective RFID sensor 1202 of the belt 1200 to allow the clinician to monitor the progress of the catheter 1100 insertion. In aspects, the display 104 (FIGS. 1 and 11) of the manometry system 100 may show a graphic of the insertion based on the information received by the belt 1200. When the distal-most RFID tag 1104 of the catheter 1100 is at the desired location (e.g., the stomach), and therefore in overlapping alignment with the distal-most RFID sensor 1202, the clinician will know that the catheter 1100 is in the correct position and may be secured in place, e.g., utilizing the strap 800 (FIGS. 7A-7B). It is contemplated that the clinician may monitor the RFID sensors 1202 and/or the display 104 (FIG. 1) while the manometry procedure is being performed to continuously verify whether the catheter 1100 is maintained in the correct position.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A manometry system, comprising:

a manometric catheter comprising:

a flexible, elongated body including a proximal end portion, and a distal end portion configured for receipt in a gastrointestinal (GI) tract of a patient;

a plurality of pressure sensors positioned along a length of the elongated body; and a plurality of RFID tags coupled to the distal end portion of the elongated body; and a belt configured to be secured to an external surface of the patient and having a length approximating a length of an esophagus and extending externally along a path corresponding to the patient's esophagus and stomach, the belt including a plurality of RFID sensors positioned along a length of the belt in axially spaced relation from one another, wherein:

the plurality of RFID sensors are configured to sequentially detect the plurality of RFID tags as the manometric catheter is advanced within the GI tract;

the manometry system is configured to determine a progress of insertion of the manometric catheter within the GI tract based on the sequential detection of the plurality of RFID tags by the plurality of RFID sensors of the belt; and positioning of the distal end portion within the stomach is determined when a distal-most RFID tag is detected by a distal-most RFID sensor of the belt.

2. The manometry system according to claim 1, wherein each of the plurality of RFID tags has a unique ID.

3. The manometry system according to claim 1, further comprising a display in communication with the belt and configured to receive the signals output from the plurality of RFID sensors and display a progress of an insertion of the manometric catheter within the GI tract.

4. The manometry system according to claim 1, further comprising:

a processor; and a memory, including instructions stored thereon, which, when executed, cause the manometry system to:

acquire a pressure measurement from each of the plurality of pressure sensors; and assess, based on the pressure measurements, at least one of a motility function of an esophagus or a bolus transit dynamics in the esophagus.

5. The manometry system according to claim 4, further comprising a remote controller configured to be in communication with the processor, the remote controller having an actuator configured to actuate functions of the manometry system.

6. The manometry system according to claim 5, wherein the remote controller includes a user interface display.

7. The manometry system according to claim 1, further comprising a flexible strap configured to secure the proximal end portion of the manometric catheter to a head of a patient.

8. A manometry system, comprising:

a manometric catheter configured to be received in a gastrointestinal (GI) tract of a patient, the manometric catheter including:

a plurality of pressure sensors positioned along a length of the manometric catheter; and a plurality of RFID tags positioned along a distal portion of the manometric catheter and axially spaced from one another, each of the plurality of RFID tags having a unique ID; and an RFID scanner configured to detect the plurality of RFID tags as the manometric catheter is advanced within the GI tract, wherein the manometry system is configured to determine a position of the manometric catheter within the GI tract based on detection of the RFID tags and identification of the unique ID of each detected RFID tag.

9. The manometry system according to claim 8, wherein the RFID scanner comprises a patch configured to be secured to an external surface of the patient and configured to detect the RFID tags when the RFID tags are within a threshold distance of the patch.

10. The manometry system according to claim 8, wherein the RFID scanner comprises a belt configured to be secured to an external surface of the patient, the belt having a length approximating a length of an esophagus and including a plurality of RFID sensors positioned along a length of the belt in axially spaced relation from one another.

11. The manometry system according to claim 10, wherein the plurality of RFID sensors are configured to sequentially detect the plurality of RFID tags as the manometric catheter is advanced within the GI tract.

12. The manometry system according to claim 11, wherein a distal end portion of the manometric catheter is determined to be positioned within a stomach of the patient when a distal-most RFID tag is detected by a distal-most RFID sensor of the belt.

13. A manometry system, comprising:

a manometric catheter configured to be received in a gastrointestinal (GI) tract of a patient, the manometric catheter including:

a plurality of pressure sensors positioned along a length of the manometric catheter; and a plurality of RFID tags positioned along a distal portion of the manometric catheter and axially spaced from one another; and a plurality of RFID scanners configured to be secured to an external surface of the patient at locations corresponding to portions of the patient's esophagus and stomach, wherein the plurality of RFID scanners are configured to detect the plurality of RFID tags as the manometric catheter is advanced within the GI tract, and wherein the manometry system is configured to determine a progress of insertion of the manometric catheter within the GI tract based on sequential detection of the RFID tags by the plurality of RFID scanners.

14. The manometry system according to claim 13, wherein each of the plurality of RFID scanners comprises a patch configured to be secured to the external surface of the patient.

15. The manometry system according to claim 14, wherein the plurality of RFID tags are spaced along the manometric catheter at predetermined distances from one another.

16. The manometry system according to claim 15, further comprising a display configured to receive signals generated by the plurality of RFID scanners and display a progress of insertion of the manometric catheter within the GI tract.

17. The manometry system according to claim 14, wherein a distal-most RFID tag corresponds to a distal end portion of the manometric catheter, and the manometry system is configured to determine that the distal end portion of the manometric catheter has reached a stomach of the patient when the distal-most RFID tag is detected by a scanner positioned at a location corresponding to the stomach.

* * * * *